United States Patent [19]
Milazzo

[11] Patent Number: 5,879,414
[45] Date of Patent: Mar. 9, 1999

[54] HYDROUS HAIR DYEING STICK COMPOSITIONS

[75] Inventor: Stefano Milazzo, Edinburgh, United Kingdom

[73] Assignee: Solid Products Limited, United Kingdom

[21] Appl. No.: 809,120

[22] PCT Filed: Sep. 6, 1995

[86] PCT No.: PCT/GB95/02115

§ 371 Date: Mar. 14, 1997

§ 102(e) Date: Mar. 14, 1997

[87] PCT Pub. No.: WO96/09031

PCT Pub. Date: Mar. 28, 1996

[30] Foreign Application Priority Data

Sep. 19, 1994 [GB] United Kingdom ................... 9418864
Feb. 13, 1995 [GB] United Kingdom ................... 9502769

[51] Int. Cl.⁶ ..................................................... A61K 7/13
[52] U.S. Cl. ........................... 8/433; 8/405; 8/435; 8/525; 8/526; 8/580; 8/585

[58] Field of Search .............................. 8/405, 429, 431, 8/433, 435, 525, 526, 527, 528, 585, 406, 580; 132/208, 318; 424/70.6, 70.7, 64

[56] References Cited

U.S. PATENT DOCUMENTS

| | | | |
|---|---|---|---|
| 313,121 | 3/1885 | Stoltz | 8/405 |
| 556,726 | 3/1896 | Andersen | 8/525 |
| 1,055,355 | 3/1913 | Richez | 8/526 |
| 1,139,326 | 5/1915 | Barrington | 8/525 |
| 2,835,604 | 5/1958 | Aronberg | 8/525 |
| 4,804,385 | 2/1989 | Grollier et al. | 8/406 |

FOREIGN PATENT DOCUMENTS

| | | |
|---|---|---|
| A 438886 | 6/1940 | Belgium . |
| A 1073335 | 9/1954 | France . |

*Primary Examiner*—Paul Lieberman
*Assistant Examiner*—Caroline D. Liott
*Attorney, Agent, or Firm*—Aslton & Bird LLP

[57] ABSTRACT

A long lasting hair-dye composition in solid stick form is described.

24 Claims, No Drawings

HYDROUS HAIR DYEING STICK COMPOSITIONS

The present invention relates to long-lasting hair dye compositions and in particular to the presentation of such compositions in solid stick form.

Conventional long-lasting hair dye compositions are generally presented in the form of a more or less thick liquid which is poured onto the hair mass, rubbed into the hair mass to distribute it through the hair mass, and then allowed to act on the hair for a period of time, perhaps up to 60 minutes depending on the dye and the temperature, to allow the dye to attach to the hair. In general the higher the temperature the shorter the time period required, thus the hair mass may, for example be covered over by a cap to trap body heat in it, or subjected to heating from a hot air blower. The residual composition is then washed out of the hair.

These known compositions are, however, somewhat awkward to apply and considerable care is required to avoid the dye running down the subject's head and possibly onto his/her clothes. Also considerable care and skill is required in order to obtain either a reasonably even distribution or a heavier application in specific sections of the hair mass for any desired special effect and/or to even out an existing unevenness in colouring.

It has also previously been proposed to provide pasty stick or slab compositions for dyeing hair in which the dyestuff is encapsulated in micro-capsules to prevent deterioration thereof prior to use, the dyestuff being released by bursting of the micro-capsules by pressing the stick against the hair to be dyed. A problem with this approach is however that the effectiveness of the dye application depends on the successful bursting of the microcapsules which in turn depends on adequate pressure being exerted by pressing hard enough against the body underlying the hair mass to be dyed. A further problem is that the surface layer of the stick will retain a quantity of broken micro-capsules and the dye released therefrom which have not been transferred to the hair mass. This dyestuff is of course no longer protected against deterioration and the surface layer will then tend to undergo various undesirable changes dye to interaction of the stick base with the dye, interaction of dye and/or other different components released from different micro-capsules, and/or interaction of the contents of the micro-capsules with the atmosphere.

It has also previously been proposed to use stick formulations with a stearic acid base. These can however suffer from poor hardness characteristics if cooling of the final mix during production is not carefully controlled, as well as from a lack of stability of the hardness characteristic in relation to temporary exposure to higher temperatures e.g. if the stick composition is subjected to higher temperature in a salon window for some time causing it to soften, the stick fails to recover its original hardness when it cools down again and becomes somewhat brittle with pieces flaking off when the stick is drawn across a head of hair resulting in uneven dye application and increased risk of dye "spillage" onto the client's clothes or surrounding floor and furniture.

Another significant drawback of a stearic acid based product is that its relatively low pH—generally around pH 5 to 5.5—results in relatively poor penetration of the dye into the hair with the result the dye is more or less rapidly lost from the hair upon washing thereof. In addition because stearic acid is relatively insoluble in water, products based on it are on the one hand more difficult to apply to hair and on the other hand more difficult to wash out when the hair dyeing treatment has been completed, as well as being more difficult to produce in a fully homogenous form.

It is an object of the present invention to avoid or minimise one or more of the above disadvantages.

The present invention provides a solid wash resistant hair colourant stick composition comprising an intimate admixture of a wash resistant hair dye with a physiologically acceptable compatible solid base having a hardness which is sufficiently high to provide substantial dimensional stability under light to moderate manual pressure under ambient temperatures and having a composition with a combination of hardness, texture, and water solubility characteristics for allowing easy gliding of the stick over a mass of damp hair and transfer of stick material thereto under light to moderate manual pressure in a generally smooth and controlled manner substantially without fracture of the stick or substantially discontinuous deposition of material.

With such a composition it has now become possible for more or less unskilled individuals to dye their own hair with, on the one hand, little risk of dye spreading onto the user's clothes, whilst on the other hand, obtaining good results with considerable control over colour intensity and distribution. Moreover the user can easily modify and/or top-up their colouring whenever required at his or her own convenience.

Preferably the stick composition also contains an effective amount of a lathering component.

The texture of the stick compositions of the invention is generally such as to have a combination of shear resistance, elasticity and flexibility so that when a user applies varying degrees of light to moderate pressure to the stick when drawing it over wet hair, the stick is substantially resistance to fracture i.e. breaking off of larger or smaller pieces of the stick, as well as being resistant to smearing i.e. irregular discontinuous deposition of stick material. Instead the stick material continues to be transferred in a substantially smooth manner, albeit that the deposition rate generally increases somewhat with increasing pressure applied by the user and when increased pressure is applied when drawing the stick across the hair, the stick end in contact with the hair can resiliently deform to a degree so as to avoid substantially fracture thereof. Specific examples of compositions with such characteristics are described in detail herein, and other suitable formulations can also be provided by means of simple trial and error in the light of the general disclosure herein as well as the general state of the art relating to cosmetic stick compositions produced for various other purposes such as deodorants, lipsticks, etc.

The present invention is applicable to various wash-resistant dyes, including so-called permanent dyes wherein the dye is permanently bound to the hair and can only be removed by cutting off of the dyed hair or by some chemical treatment. Where such dyes are used then there will normally be required an oxidising agent. Thus, for example, the hair could be wetted with a peroxide solution prior to drawing the stick composition over it.

The present invention is however particularly suitable for use with so-called semi-permanent dyes wherein the dye-stuff is bound more or less firmly to the hair so that it is substantially resistant to washing out, but nevertheless is progressively lost from the hair, generally having an effective half-life of several washes e.g. from 5 to 10 washes, and usually becoming completely washed out after about 20 washes, when good hair penetration by the dye has been achieved. It will be appreciated that the degree of penetration of the dye into the hair will depend on the inter alia amount of swelling of the hair attained. Where a suitable lathering component is used (as described in more detail hereinbelow) then this itself can provide a substantial degree of hair swelling. In other cases there may be used a lathering component such as a soap (which may also serve as a hardness component in the solid base), which has only a limited effect on swelling of hair. In such cases there may advantageously be included a specific hair swelling agent such as urea in order to increase hair swelling sufficiently to achieve good dye penetration. It may also be noted that use of ammonium compounds (e.g. an ammonium salt such as ammonium stearate or an ammonium detergent such as ALS) in an alkaline stick will tend to give increased hair swelling as compared with alkali metal forms of these due to the presence of free ammonia. Nevertheless this is not essential albeit that it should be appreciated that where only limited swelling is achieved, then dye penetration will be restricted and the wash resistance of the hair colouring achieved may be limited to just a small number of washes.

One advantage of such a system is that of substantially avoiding highly visible "dyeing lines" at the boundary between dyed and newly grown undyed hair and allowing colour to be more or less readily changed without undue delay. A particular advantage is moreover, that as soon as the user perceives that the dye has faded to an unacceptable degree after a number of washes, the required colour intensity can readily be restored by the user himself or herself in a simple and effective manner with a stick composition of the present invention.

A principal component of the solid base responsible for the hardness thereof is advantageously a water soluble salt of a higher alkyl carboxylic fatty acid, usually a C14 to C18 e.g. palmitic acid or oleic acid, but most preferably stearic acid. Preferably there is used a salt from a relatively strong alkali so that an aqueous solution of the salt is alkaline, preferably with a pH of at least 8. Suitable salts include sodium, potassium and ammomium salts. A particular advantage of using such water soluble salts in the base is that their water solubility significantly facilitates transfer of the composition to hair—even where this is only slightly damp, with a smooth gliding action of the stick which is both easier on the hairdresser and the client. This is moreover true even when the hardness of the stick is very high. Thus it will be appreciated therefore that the composition of the stick base can be varied to produce different combinations of hardness, texture, and water solubility which together provide the required smooth gliding and controlled transfer characteristics.

The use of a lathering component helps to provide an even and effective distribution of the stick material deposited on the hair, across the whole mass of hair which is being dyed and thus facilitate a substantially even application of the dye material to the mass of hair being dyed whether it be the whole head of hair or only a selected clump of hair. This is of particular significance in the context of self-application by inexpert users and helping such users to achieve good even dye application.

Another advantage of such a base is that it is significantly more temperature stable than a fatty acid base. Thus, for example, whereas a stearic acid base tends to soften at 25° C. to 30° C. i.e. moderate ambient temperatures, a sodium stearate base can substantially maintain its hardness up to around 40° C. A stearate base is also generally better able to achieve and maintain the described combination of hardness and texture for smooth controlled material application.

The fatty acid salt is normally used together with an effective amount of a hardness control agent. It has been found that the hardness of the stick composition depends substantially on the fatty acid salt and amount thereof used, as well as on the particular liquid dispersed and/or direct dye component used. Various suitable hardness control agents may be used to bring the hardness of the solid base within the desired range.

Advantageously there is used a hardness control agent which comprises a substantially non-volatile and water soluble monohydric or polyhydric, (optionally substituted) alcohol, preferably a lower alkyl aliphatic alchol. Desirably there is used a C3 to C8 monohydric or polyhydric alchol or derivative having a low vapour pressure at ambient temperatures. Suitable examples that may be mentioned include propylene glycol, ethoxydiglycol, butylene glycol, glycerol, and polyethylene glycols such as PEG-15-glyceryl laurate. Suitable alcohols also have humectant properties and help to reduce moisture loss form the stick and thus increase effective shelf-life.

The hardness and water solubility of the compositions may also be controlled by incorporating water therein to a greater or lesser degree. Indeed it is possible to incorporate up to around 80%, preferably from 10 to 75%, by weight of water.

If desired there may also be included a longer chain aliphatic alcohol or derivative thereof such as, for example, one or more of cetyl alcohol, stearyl alcohol, glycol stearate, and coconut mono-ethanolamide.

As noted above there is advantageously used a principal base component which is alkaline, desirably having a pH value in aqueous solution of from 8 to 10, advantageously from 8.5 to 9.5, e.g. about 9. With such an alkaline base there is obtained an increased and longer-lasting dye uptake as the alkaline pH contributes to swelling of the hair thereby allowing easier penetration and absorption of the dye into the hair and better retention when the hair shrinks back to its normal form after washing out of the dye composition. Thus where a higher pH value is used it may be possible to reduce the amount of other components used to induce hair swelling, if desired.

Various forms and shapes of solid stick composition may be used including generally cylindrical stick and flattened bar forms. It will be understood that the hardness of such a composition can be measured by various methods generally known in the art. Preferably the solid composition has a hardness of at least 4, advantageously in the range from 4 to 30, most preferably from 4 to 25 Newtons when measured by the following method. An Instron Universal Testing Instrument 1122 (normally used for testing the hardness of stick compositions such as lipstick) was employed with a steel probe having a diameter of 7 mm. The solid composition is placed in a holder and the probe advanced towards the stick at a rate of 50 mm/minute. When the probe tip contacts the surface of the solid composition it experiences a resistance to continued forward movement requiring the probe driving force to be increased. This force continues to increase to a peak when the probe breaks-through into the interior of the solid composition and this initial peak is used to provide a measure of the hardness of the solid composition.

It will be appreciated by those skilled in the art that the hardness range referred to above is relatively broad and indeed, as already noted above, substantially greater hardnesses can be used where the stick has a suitable texture and/or, in particular, good water solubility. This is possible with a substantially water-soluble base such as those described hereinbefore, which glide easily over the hair, and provides increased tolerance and flexibility in manufacture of compositions of the present invention.

As used herein the term "compatible" means that the solid base should not have a significant adverse effect on the performance and functioning of the hair dye, in particular in relation to its colour, its effective life both on the shelf and in the hair i.e. its ability to penetrate the hair, to become attached thereto, and to withstand substantially at least a number of hair washes, and non-colouring of the scalp or skin generally.

The new stick compositions of the present invention can be readily applied to a wetted head of hair by simply drawing the stick more or less gently over the hair as required. It will be appreciated that the application of the hair colourant is particularly easy and convenient to control as the stick can be drawn over different parts of the hair mass as many times as may be required for any given part of the hair mass, without the risk of a liquid composition running down the subject's neck etc. Where it is desired to achieve a particular effect then it is possible to separate a selected clump of hair from the rest, draw the stick over this clump, and rub the composition into the sected part only (see below).

Once the required amount of composition has been applied, it can be rubbed into the hair mass (with additional moistening of the hair if required e.g. by spraying on some water) to work it into the hair mass. As noted hereinbefore, the stick composition of the present invention includes a lathering component which may conveniently be in the form of a shampoo-type base which can be worked up into a lather by the rubbing in at this stage. A suitable lathering component that may be mentioned is ammonium lauryl sulphate though various other detergents may also be used including anionic and cationic detergents, and tallow based surfactants, care being taken to ensure compatibility with the dye components being used. Conveniently there is used from 2.5 to 18% w/w, preferably from 8 to 14.5% w/w, of the lathering component (active form) in the composition. The composition is then left in place for some time to allow the dye component(s) to become attached to the hair. The required time will depend on factors such as the particular dye components used and the temperature, increased temperatures generally requiring less time as noted hereinabove. Suitable times will generally be in the range from as little as 2 to 3 minutes in some cases and generally from 10 to 60 minutes or so. The residual composition can then be washed out in the normal way and the hair dried.

Various dyes may be used in the stick compositions of the present invention including permanent and semi-permanent dyes of various types such as direct and dispersed type dyes. Preferably there are used so-called "direct" dyes which bond physically e.g. electrostatically to the hair fibres, without the need for any chemical reaction, e.g. oxidation, taking place, and can produce a semi-permanent colouring of the hair which can withstand several hair-washes before substantial loss of colour occurs. Various suitable direct dyes are known in the art including so-called dispersed dyes, acidic dyes, and basic dyes.

The amounts of solid base may be varied according to the final consistency and ease of application required and will also depend on the nature of the liquid dye composition used and the intensity of dyeing required, and the particular solid base used. In general the stick compositions of the invention may contain from 10 to 90% w/w, preferably from 50 to 80% w/w of the liquid hair dye composition (including any shampoo-type base etc), and from 10 to 90% w/w, preferably from 30 to 70% w/w of the solid base.

The amounts of fatty acid salt hardener thickening agent and of the hardness control agent may be varied according to the final consistency and ease of application required and will also depend on the nature of the liquid dye composition used, and the particular combination of thickening and hardness control agents. In general the stick compositions of the invention may contain from 40 to 90% w/v, preferably from 50 to 80% w/v of the liquid hair dye composition (including any shampoo-type base etc), from 5 to 30% w/w, preferably from 6 to 20% w/w, most preferably from 8 to 15% w/w of the fatty acid salt thickening agent, and from 3 to 30% w/w, preferably from 4 to 20% w/w, most preferably from 5 to 10% w/w of the hardness control agent.

It will be appreciated that various liquid hair dye compositions which are readily available commercially, may be used in the stick compositions of the present invention. These may include various conventionally employed materials as desired such as for example chelating agents such as EDTA to minimise scum formation when the composition is used with hard water and/or heavily mineralised water: emulsifying and/or stabilising agents such as ethoxydiglycol; additional surfactants e.g. tallow based surfactants such as ammonium lauryl sulphate, e.g. that commercially available as Lowenol 1985™ available from Lowenstein Dyes & Cosmetics Inc. of New York, U.S.A; and thickening agents such as chemically modified cellulose polymers e.g. Cellow 940™ also available from Lowenstein and sodium carboxymethylcellulose. The amount of individual dye(s) used will generally depend on the intensity of colouring required. If desired some water can be included to facilitate incorporation of the dye into the composition, and/or to help "dilute" the intensity of the colouring produced by the dye.

Other suitable ingredients may also be incorporated in the compositions of the present invention in generally known manner. Thus, for example, there may be included a physiologically acceptable preservative. Suitable preservatives that may be mentioned include "Kathon"™ which comprises methyl chloroisothiazolinone, methyl isothiazolinone, and magnesium nitrate; or a mixture of methyl paraben and propyl paraben. Advantageously there may also be included hair conditioning agents such as polyquaternium compounds and/or an enhancing agent such as dimethicone (dimethyl polysiloxane) which improves shine in the hair and the vibrancy of the colouring thereof. In order to increase the uptake of dye into grey hair there may advantageously be included a hair swelling agent such as urea. Preferably this is used in an amount of from 2 to 6% preferably about 5% w/w.

The compositions of the invention may be prepared by any suitable method known in the art. Conveniently the hardening medium component(s) is (are) heated to an elevated temperature at which it is (they are) substantially fluid without being adversely affected e.g. from 55° to 70° C., and homogenized if required. The other ingredients are then added at a generally similar elevated temperature and thoroughly mixed in. The resulting mixture may be cooled slightly, e.g. to around 50° to 60° C., and then poured into a suitable mould or directly into a holder or container for the stick, and allowed to cool and solidify.

In yet another aspect the present invention provides a method of dyeing hair comprising the steps of:

wetting the hair;

drawing a stick composition of the invention across said hair under light to moderate manual pressure so as to transfer material from the stick composition on to the hair;

rubbing the said material into the wetted hair so as to produce a lather in the hair;

allowing the dye from said composition to penetrate the hairs; and washing residual material out of the hair.

The present invention also provides a long-lasting solid hair colourant composition comprising an intimate admixture of a dye with a physiologically acceptable compatible solid base having a hardness which is sufficiently high to provide substantial dimensional stability under light to moderate manual pressure under ambient temperatures and sufficiently low to allow easy gliding of the stick over a mass of damp hair and transfer of stick material thereto under light to moderate manual pressure, and containing an effective lathering component, whilst being substantially free of stearic acid.

Further preferred features and advantages of the present invention will appear from the following examples given by way of illustration only.

EXAMPLE 1
Preparation of Hair Dye Stick Composition
A. Preparation of Liquid Shampoo-Base Dye Composition A generally conventional shampoo—in dye composition was prepared with the following ingredients which are readily available from Companies such as Lowenstein Dyes & Cosmetics Inc of New York.

Dyestuff
- HC Blue 2 Solid 44.0 g
- Lowadene Violet 1 10.0 g
- Lowadene Black 9 13.0 g
- HC Yellow 4 2.750 g
- HC Red 3 0.440 g
- Lowalan Orange 3 5.0 g
- Lowadene Orange 3 0.90 g
- Lowadene Blue 61505 8.760 g
- Lowadene Blue 62500 6.190 g Shampoo Base
- Ethoxydiglycol 50.0 g
- Deionized Water 320.0 g
- Lowenol 1985 Surfactant 120.0 g
- Cellow 940 (2% aqueous solution) thickener 500.00 g
- Kelene Na 4 (EDTA) 6.0 g
- Monoethanolamine (as required to adjust pH)

The dye composition was dissolved in the water and exthoxydiglycol with stirring at 50°–60° C. and the Lowenol 1985 then added, followed by the Cellow 940 and Kelene Na 4. The pH of the resulting viscous liquid was then adjusted to 8.7 0.2 by adding monoethanolamine as required.

B Solidification of Dye Composition

Sodium Stearate (micronized 110–170 g.) was added with stirring at 65°–70° C., followed by glycerol (70–120 g) (or alternatively a similar amount of butylene glycol). The final mixture was stirred for some 2–3 minutes and the hot fluid then poured into moulds and cooled in a cooling chamber.

It will be appreciated that various modifications may be made to the above embodiment without depending from the scope of the present invention. Thus, for example, instead of micronized sodium stearate there may be used a beaded form, with that available under the identification "B2" from the Megret Company being particularly suitable.

EXAMPLE 2
Use of hair Dye stick

The hair dye stick produced in Example 1 was stroked over a pre-wetted head of hair until a visible amount of the composition had been applied across substantially the whole of the hair mass. A small amount of water was then sprayed onto the hair and composition was then gently rubbed in for 3 to 4 minutes building up a substantial lather. The hair mass was heated with a hair dryer for about 20 minutes, and then rinsed in warm water. The hair was then shampoo-washed in the normal way and towelled dry.

EXAMPLE 3
Preparation of Hair Dye Stick Composition

A 100 g stick composition was prepared with the following composition:
- CARBITOL 3.7 g
- 1,3-BUTYLENE GLYCOL 7.03 g
- NATROSOL 250 HR 0.4 g
- SEQUESTRENE NA4 0.44 g
- LOWENOL 1985 8.88 g
- SODIUM STEARATE B2 12.57 g
- HC YELLOW 2 0.19 g
- HC BLUE 2 CP 0.94 g
- HC RED 3 0.22 g
- PURIFIED WATER BP TO 100 g The purified water, butylene glycol, and sequestrene were added together with stirring. Whilst continuing mixing the carbitol was added, followed by slow addition of the natrosol (which had been premixed with part of the water) and mixing continued until the latter was fully hydrated.

The mixture was then warmed to 60°–65° C. Mixing was then stopped and the Lowenol surfactant added taking care to avoid aeration. Stirring was then resumed and the temperature adjusted to between 60°–65° C. and the dyestuff components then added, with stirring continued for an additional 10 minutes.

The temperature was then raised to between 65°–70° C. and the Sodium Stearate then added slowly with stirring. The temperature was readjusted to maintain it between 65°–70° C. and mixing continued until the mixture was completely homogeneous. Whilst continuing slow stirring the mixture was then cooled to around 50° C. whereupon it was introduced into a generally cylindrical mould or holder and allowed to cool to ambient temperature to form a solid stick.

I claim:

1. A hydrous solid wash resistant hair colorant stick composition comprising an intimate admixture of:
    10 to 80% w/w water;
    a wash resistant hair dye; and
    a physiologically acceptable compatible solid base comprising 5 to 30% w/w of a water soluble salt of a higher alkyl carboxylic fatty acid and 3 to 30% w/w of a hardness control agent, said hair dye being in intimate contact with said solid base, wherein said stick composition has a hardness which is sufficiently high to provide substantial dimensional stability under light to moderate manual pressure under ambient temperatures and having a composition with a combination of hardness, and water solubility characteristics for allowing easy gliding of the stick over a mass of damp hair and transfer of stick material thereto under light to moderate manual pressure in a generally smooth and controlled manner substantially without fracture of the stick or substantially discontinuous deposition of material.

2. A composition according to claim 1 which includes from 10 to 75% by weight of water.

3. A composition according to claim 1 which includes an effective amount of a lathering component.

4. A composition according to claim 1 wherein said hair dye is a semi-permanent dye.

5. A composition according to claim 1 which has a hardness of at least 4 Newtons when measured with an Instron Universal Testing Instrument 1122 to advance a steel probe having a diameter of 7 mm towards the solid composition at a rate of 50 mm/minute until the probe breaks through into the interior of the solid composition.

6. A composition according to claim 1 wherein said acid is selected from the group consisting of palmitic, oleic and stearic acids.

7. A composition according to claim 6 wherein said acid is stearic acid.

8. A composition according to claim 1 further comprising a salt from a strong alkali, which salt has a pH in aqueous solution of from 8 to 10.

9. A composition according to claim 8 wherein said salt from a strong alkali is selected from the group consisting of ammonium salts and alkali metal salts.

10. A composition according to claim 1 wherein said hardness control agent comprises a substantially non-volatile alcohol or derivative thereof.

11. A composition according to claim 10 wherein said alcohol is a long-chain aliphatic alcohol or derivative thereof.

12. A composition according to claim 11 wherein said alcohol is cetyl alcohol.

13. A composition according to claim 10 wherein said alcohol is a glycol.

14. A composition according to claim 1 which includes an emulsifier.

15. A composition according to claim 3 wherein said lathering component comprises a detergent.

16. A composition according to claim 3 which contains from 2.5% to 18% w/w of said lathering component.

17. A composition according to claim 3 which contains from 10 to 90% w/w of the wash resistant hair dye and lathering component and from 90 to 10% w/w of the solid base.

18. A composition according to claim 1 which includes a hair swelling agent.

19. A composition according to claim 3 wherein said lathering component has an effective hair swelling capability.

20. A composition according to claim 18 wherein said hair swelling agent is urea.

21. A composition according to claim 1 which is substantially free of stearic acid.

22. A method of dyeing hair comprising the steps of:
   wetting the hair;
   drawing a stick composition according to claim 1 across said hair under light to moderate manual pressure so as to
   transfer material from the stick composition on to the hair;
   rubbing the said material into the wetted hair;
   allowing the dye from said composition to penetrate the hairs; and
   washing residual material out of the hair.

23. A method according to claim 22 wherein said composition contains an effective amount of a lathering component, and in which method said material transferred to the hair is rubbed in so as to produce a lather in the hair.

24. A composition according to claim 19 comprising urea as a hair swelling agent.

* * * * *

UNITED STATES PATENT AND TRADEMARK OFFICE
CERTIFICATE OF CORRECTION

PATENT NO. : 5,879,414                                Page 1 of 2

DATED : March 9, 1999

INVENTOR(S) : Milazzo

It is certified that error appears in the above-identified patent and that said Letters Patent is hereby corrected as shown below:    On the title page, item [56]

In the References Cited, U.S. PATENT DOCUMENTS, insert the following:

--4,695,452   9/1987   Gannis et al.

4,147,750   4/1979   Geria et al.

4,286,890   9/1981   Dickmann et al.--.

In the References Cited, FOREIGN PATENT DOCUMENTS, insert the following:

--749045         5/1956    Great Britain 1288128        9/1972    Great Britain

GB2019446A   10/1979   Great Britain 2320772        3/1977    France 0117070        8/1984    Europe 0222525A2     5/1987    Europe

WO 95/20941  8/1995    PCT

WO 92/15280  9/1992    PCT

JP 59021608   2/1984    Japan 1073335        9/1954    Great Britain --

UNITED STATES PATENT AND TRADEMARK OFFICE
CERTIFICATE OF CORRECTION

PATENT NO. : 5,879,414
DATED : March 9, 1999
INVENTOR(S) : Milazzo

It is certified that error appears in the above-identified patent and that said Letters Patent is hereby corrected as shown below:

In the References Cited, insert the following:

--       OTHER PUBLICATIONS

Patent Abstracts of Japan, Vol. 8, No. 106 (JP59021608), February 3, 1984.

Patent Abstract, JP 72045502 (Derwent World Patents Index), 1972.

English translation of description WO 92/15280, 9/1992.--.

Signed and Sealed this

Twenty-seventh Day of July, 1999

Q. TODD DICKINSON

*Attest:*

*Attesting Officer*      Acting Commissioner of Patents and Trademarks